US00PP22160P2

(12) United States Plant Patent
Wood

(10) Patent No.: US PP22,160 P2
(45) Date of Patent: Sep. 27, 2011

(54) ***CARYOPTERIS* PLANT NAMED 'JANICE'**

(50) Latin Name: *Caryopteris×clandonensis*
Varietal Denomination: Janice

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,628

(22) Filed: Sep. 9, 2010

(51) Int. Cl.
*A01H 5/00* (2006.01)

(52) U.S. Cl. ..... Plt./226

(58) Field of Classification Search ..... Plt./226
See application file for complete search history.

*Primary Examiner* — Kent L Bell
(74) *Attorney, Agent, or Firm* — C. A. Whealy

(57) ABSTRACT

A new and distinct cultivar of *Caryopteris* plant named 'Janice', characterized by its compact and low mounding plant habit; vigorous growth habit; freely branching habit; full and dense plants; yellow green-colored leaves that do not burn under full sun conditions; freely flowering habit; and violet blue-colored flowers that are held above and beyond the foliar plane.

2 Drawing Sheets

Botanical designation: *Caryopteris×clandonensis.*
Cultivar denomination: 'JANICE'.

BACKGROUND OF THE INVENTION

The present invention relates to a new and distinct cultivar of *Caryopteris* plant, botanically known as *Caryopteris× clandonensis*, and hereinafter referred to by the name 'Janice'.

The new *Caryopteris* plant is a product of a planned breeding program conducted by the Inventor in Grand Haven, Mich. The objective of the breeding program is to create new compact, freely-flowering and vigorous *Caryopteris* plants with attractive leaf and flower coloration.

The new *Caryopteris* plant originated from a cross-pollination made by the Inventor in August, 2005 in Grand Haven, Mich. of *Caryopteris×clandonensis* 'Minibleu', disclosed in U.S. Plant Pat. No. 14,674, as the female, or seed, parent with *Caryopteris×clandonensis* 'Jason', disclosed in U.S. Plant patent application Ser. No. 10/878,606 (Abandoned), as the male, or pollen, parent. The new *Caryopteris* plant was discovered and selected by the Inventor as a single flowering plant within the progeny of the stated cross-pollination in a controlled environment in Grand Haven, Mich. during the summer of 2007.

Asexual reproduction of the new *Caryopteris* plant by softwood cuttings in a controlled environment in Grand Haven, Mich. since June, 2007, has shown that the unique features of this new *Caryopteris* plant are stable and reproduced true to type in successive generations.

SUMMARY OF THE INVENTION

The cultivar Janice has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Janice'. These characteristics in combination distinguish 'Janice' as a new and distinct cultivar of *Caryopteris* plant:

1. Compact and low mounding plant habit.
2. Vigorous growth habit.
3. Freely branching habit; full and dense plants.
4. Yellow green-colored leaves that do not burn under full sun conditions.
5. Freely flowering habit.
6. Violet blue-colored flowers that are held above and beyond the foliar plane.

Plants of the new *Caryopteris* can be compared to plants of the female parent, 'Minibleu'. Plants of the new *Caryopteris* differ from plants of 'Minibleu' primarily in leaf coloration as plants of 'Minibleu' have dark green-colored leaves.

Plants of the new *Caryopteris* can be compared to plants of the male parent, 'Jason'. Plants of the new *Caryopteris* differ from plants of 'Jason' in the following characteristics:

1. Plants of the new *Caryopteris* are more compact than plants of 'Jason'.
2. Plants of the new *Caryopteris* are denser than and not as open as plants of 'Jason'.
3. Leaves of plants of the new *Caryopteris* are glossier than leaves of plants of 'Jason'.

Plants of the new *Caryopteris* can be compared to plants of *Caryopteris incana* 'Worcester Gold', not patented. In side-by-side comparisons conducted in Grand Haven, Mich., plants of the new *Caryopteris* differed from plants of 'Worcester Gold' in the following characteristics:

1. Plants of the new *Caryopteris* were more compact than plants of 'Worcester Gold'.
2. Plants of the new *Caryopteris* were more uniform than plants of 'Worcester Gold'.
3. Plants of the new *Caryopteris* are more freely branching and denser than plants of 'Worcester Gold'.
4. Leaves of plants of the new *Caryopteris* were glossier than leaves of plants of 'Worcester Gold'.
5. Leaves of plants of the new *Caryopteris* did not burn under full sun conditions whereas leaves of plants of 'Worcester Gold' burned under full sun conditions.

BRIEF DESCRIPTION OF THE PHOTOGRAPHS

The accompanying colored photographs illustrate the overall appearance of the new *Caryopteris* plant showing the colors as true as it is reasonably possible to obtain in colored reproductions of this type. Colors in the photographs may differ slightly from the color values cited in the detailed botanical description which accurately describe the colors of the new *Caryopteris* plant.

The photograph on the first sheet comprises a side perspective view of a typical flowering plant of 'Janice' grown in an outdoor nursery.

The photograph on the second sheet is a close-up view of a typical flowering plant of 'Janice'.

DETAILED BOTANICAL DESCRIPTION

The aforementioned photographs and following observations and measurements describe plants grown during the summer in an outdoor nursery in Grand Haven, Mich. Plants were two years old when the photographs and description were taken. In the following description, color references are made to The Royal Horticultural Society Colour Chart, 2001 Edition, except where general terms of ordinary dictionary significance are used.

Botanical classification: *Caryopteris×clandonensis* 'Janice'.

Parentage:

*Female, or seed, parent.*—*Caryopteris×clandonensis* 'Minibleu', disclosed in U.S. Plant Pat. No. 14,674.

*Male, or pollen, parent.*—*Caryopteris×clandonensis* 'Jason', disclosed in U.S. Plant patent application Ser. No. 10/878,606 (Abandoned).

Propagation:

*Type.*—By softwood cuttings.

*Time to initiate roots, summer.*—About 20 days at 24° C.

*Time to produce a rooted young plant, summer.*—About three months at 24° C.

*Root description.*—Fine, fibrous; creamy white in color.

*Rooting habit.*—Freely branching; dense.

Plant description:

*Plant form and habit.*—Perennial deciduous shrub; compact and low mounding plant habit; freely branching habit with about 347 lateral branches developing per plant; full and dense plant habit; vigorous growth habit.

*Plant height.*—About 35 cm.

*Plant diameter.*—About 40 cm.

Lateral branch description:

*Length.*—About 17 cm.

*Diameter.*—About 2 mm.

*Internode length.*—About 2 cm.

*Strength.*—Strong.

*Texture.*—Pubescent.

*Color, developing branches.*—Close to 145A and 181A.

*Color, developed branches.*—Close to 199B.

Foliage description:

*Arrangement.*—Opposite, simple.

*Fragrance.*—Aromatic.

*Length.*—About 6 cm.

*Width.*—About 1.9 cm.

*Shape.*—Lanceolate to elliptic.

*Apex.*—Obtuse.

*Base.*—Cuneate.

*Margin.*—Crenate to lobed.

*Texture, upper and lower surfaces.*—Smooth, glabrous.

*Venation pattern.*—Pinnate; arcuate.

*Color.*—Developing leaves, upper surface: Close to 1A. Developing leaves, lower surface: Close to 1B. Fully expanded leaves, upper surface: Close to 150A; venation, close to 150A, leaves do not burn under full sun conditions. Fully expanded leaves, lower surface: Close to 160A; venation, close to 160A.

*Petiole.*—Length: About 1 cm. Diameter: About 1 mm. Texture, upper and lower surfaces: Pubescent. Color, upper and lower surfaces: Close to 150A.

Flower description:

*Flower arrangement and habit.*—Solitary funnelform flowers arranged in terminal and axially panicled cymes; flowers face mostly upward or outward; freely flowering habit with about 13 flowers per inflorescence and about 104 flowers per lateral branch.

*Natural flowering season.*—Plants flower from August to October in Grand Haven, Mich., flowering continuous during this period.

*Flower longevity on the plant.*—Flowers last about eight weeks; flowers not persistent.

*Fragrance.*—None detected.

*Inflorescence height.*—About 2.2 cm.

*Inflorescence diameter.*—About 2 cm.

*Flowers.*—Appearance: Funnelform, corolla fused and five-parted. Diameter: About 2 mm. Depth (height): About 3.5 cm.

*Flower buds.*—Length: About 2 mm. Diameter: About 1 mm. Shape: Ovoid. Color: Close to 193A.

*Corolla.*—Arrangement: Single whorl of five fused petals; one larger than the other four. Petal length, largest petal: About 3 mm. Petal length, smaller four petals: About 2 mm. Petal width, largest petal: About 3 mm. Petal width, smaller four petals: About 2.5 mm. Petal lobe shape, largest petal: Oblong. Petal lobe shape, four smaller petals: Ovate. Petal lobe apex, largest petal: Lacerate, fringed. Petal lobe apex, four smaller petals: Acute. Petal lobe margin, largest petal: Lacerate. Petal lobe margin, four smaller petals: Entire. Petal texture, upper and lower surfaces: Smooth, glabrous. Color: When opening, upper and lower surfaces: Close to 95C. Fully opened, upper and lower surfaces: Close to 95C; color becoming closer to 95D with development.

*Calyx.*—Arrangement: Single whorl of six fused sepals; calyx funnelform. Length: About 2 mm. Diameter: About 1 mm. Sepal apex: Acute. Sepal margin: Entire. Sepal texture, upper and lower surfaces: Smooth, glabrous. Sepal color, upper surface: Close to 146B. Sepal color, lower surface: Close to 195A.

*Peduncles.*—Length: About 1.2 cm. Diameter: About 1.5 mm. Strength: Strong. Texture: Smooth, glabrous. Color: Close to 146D.

*Pedicels.*—Length: About 3 mm. Diameter: About 1 mm. Strength: Strong. Color: Close to 146D.

*Reproductive organs.*—Stamens: Quantity/arrangement: Four per flower. Anther shape: Round. Anther length: Less than 1 mm. Anther color: Close to 96A. Pollen amount: Scarce. Pollen color: Close to 96A. Pistils: Quantity: One per flower. Stigma shape: Rounded. Stigma color: Close to 96D. Style length: About 1.3 cm. Style color: Close to 96D. Ovary color: Close to 195A. Seeds: Appearance: Dust-like. Length: Less than 1 mm. Diameter: Less than 1 mm. Color: Brown.

Temperature tolerance: Plants of the new *Caryopteris* have been observed to tolerate temperatures ranging from about −27° C. to about 34° C.

Pathogen/pest resistance: Plants of the new *Caryopteris* have not been observed to be resistant to pests and pathogens common to *Caryopteris* plants.

It is claimed:

1. A new and distinct *Caryopteris* plant named 'Janice' as illustrated and described.

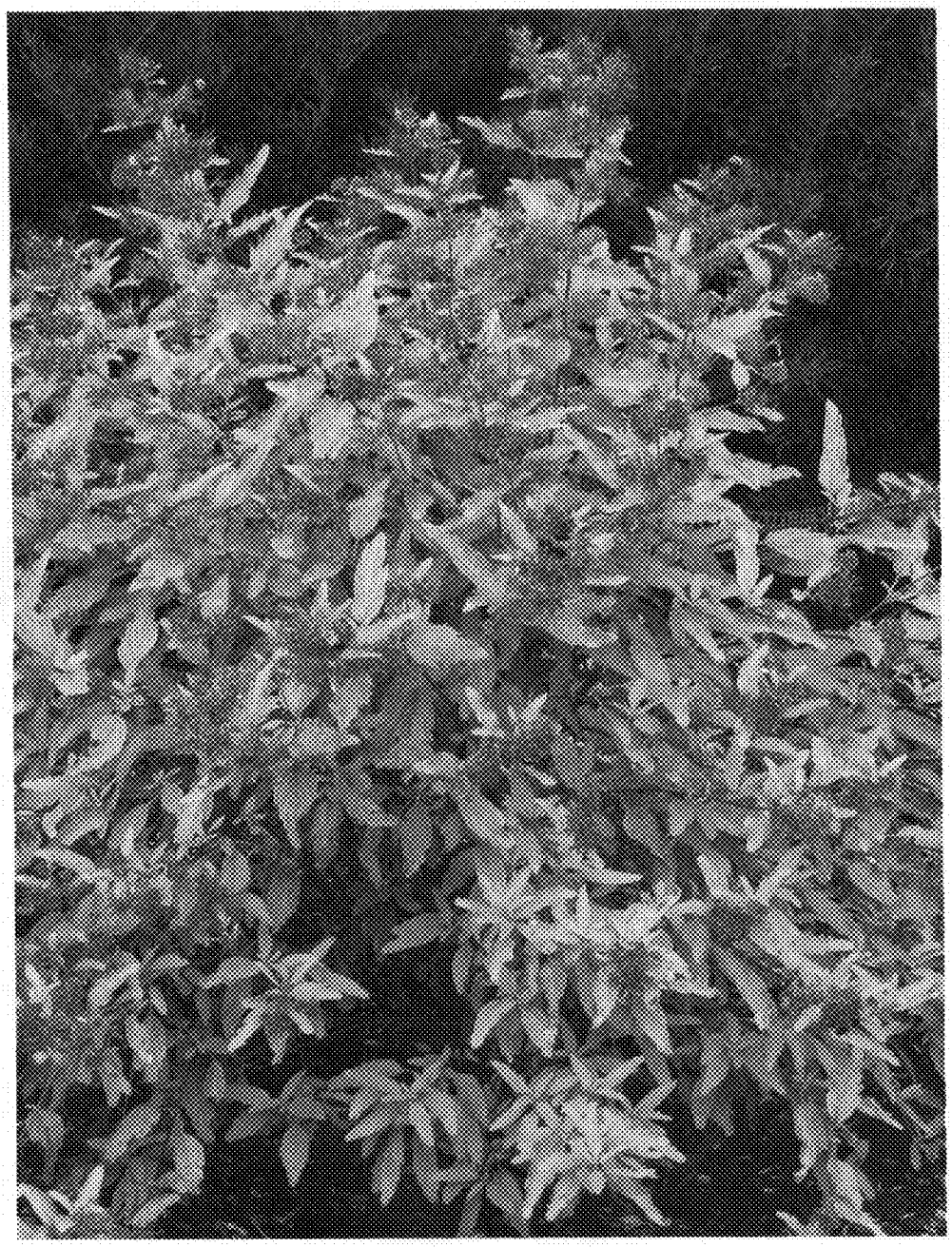

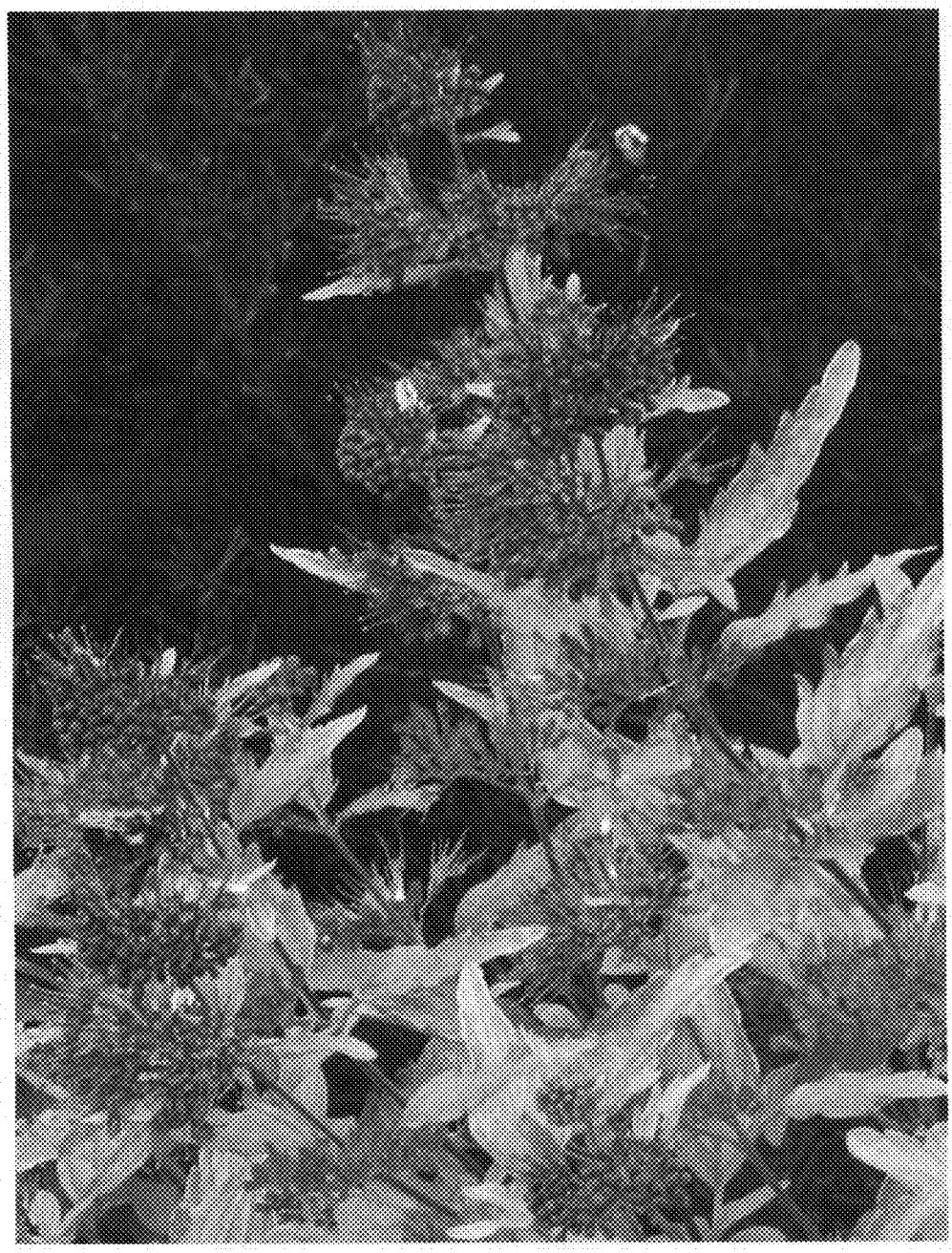

* * * * *